US011331329B2

(12) United States Patent
Morrow et al.

(10) Patent No.: US 11,331,329 B2
(45) Date of Patent: May 17, 2022

(54) FUCOSYLATED OLIGOSACCHARIDES FOR PREVENTION OF CORONAVIRUS INFECTION

(71) Applicant: Glycosyn LLC, Waltham, MA (US)

(72) Inventors: Ardythe L. Morrow, Cincinnati, OH (US); David S. Newburg, Newtonville, MA (US); John M. McCoy, Reading, MA (US)

(73) Assignee: Glycosyn LLC, Waltham, MA (US)

( * ) Notice: Subject to any disclaimer, the term of this patent is extended or adjusted under 35 U.S.C. 154(b) by 0 days.

(21) Appl. No.: 17/320,152

(22) Filed: May 13, 2021

(65) Prior Publication Data

US 2021/0353654 A1    Nov. 18, 2021

Related U.S. Application Data

(60) Provisional application No. 63/024,464, filed on May 13, 2020.

(51) Int. Cl.
| | | |
|---|---|---|
| A61K 31/702 | (2006.01) | |
| A61P 31/14 | (2006.01) | |
| A23C 9/20 | (2006.01) | |
| A23L 33/125 | (2016.01) | |

(52) U.S. Cl.
CPC ............ *A61K 31/702* (2013.01); *A23C 9/206* (2013.01); *A23L 33/125* (2016.08); *A61P 31/14* (2018.01); *A23V 2002/00* (2013.01)

(58) Field of Classification Search
CPC ..... A61K 31/702; A23L 33/125; A61P 31/14; A23C 9/206; A23V 2002/00
USPC ......................................................... 514/61
See application file for complete search history.

(56) References Cited

U.S. PATENT DOCUMENTS

| | | | |
|---|---|---|---|
| 7,893,041 B2 | 2/2011 | Morrow et al. | |
| 8,277,835 B2* | 10/2012 | Boehm | A61P 25/00 424/439 |
| 2009/0047272 A1 | 2/2009 | Appelbaum et al. | |
| 2016/0287618 A1* | 10/2016 | Sprenger | A61K 35/741 |
| 2017/0081353 A1 | 3/2017 | McCoy et al. | |
| 2017/0136049 A1 | 5/2017 | Newburg et al. | |
| 2017/0306373 A1 | 10/2017 | Heidtman et al. | |
| 2018/0036327 A1 | 2/2018 | Mcconnell et al. | |
| 2019/0218582 A1 | 7/2019 | Mallipeddi et al. | |
| 2019/0255083 A1 | 8/2019 | Newburg et al. | |
| 2020/0080119 A1 | 3/2020 | Merighi et al. | |
| 2020/0087691 A1 | 3/2020 | Heidtman et al. | |
| 2020/0190548 A1 | 6/2020 | Merighi et al. | |
| 2021/0353653 A1 | 11/2021 | Morrow et al. | |

FOREIGN PATENT DOCUMENTS

| | | |
|---|---|---|
| WO | 2013032674 A1 | 3/2013 |
| WO | 2019106620 A1 | 6/2019 |
| WO | 2019121929 A1 | 6/2019 |

OTHER PUBLICATIONS

Glossary of medical education terms, Institute of International Medical Education. http://www.iime.org/glossary.htm Accessed in Mar. 2013. (Year: 2013).*
Green M. Jennewein Biotechnology flags HMOs' potential in inhibiting infectious diseases. NutritionInsight May 28, 2020. (Year: 2020).*
Le Pendu J. Histo-Blood Group Antigen and Human Milk Oligo Saccharides: Genetic Polymorphism and Risk of Infectious Diseases. Protecting Infants through Human Milk, edited by Pickering et al., 2004, pp. 135-143. (Year: 2004).*
Watanabe et al. Site-specific analysis of the SARS-CoV-2 glycan shield. bioRxiv preprint, this version posted Mar. 28, 2020. doi:https://doi.org/10.1101/2020.03.26.010322 (Year: 2020).*
Abdul-Rasool et al., (May 25, 2010) "Understanding Human Coronavirus HCoV-NL63", The Open Virology Journal, 4:76-84.
Charlwood et al. (Sep. 1999) "A Detailed Analysis of Neutral and Acidic Carbohydrates in Human Milk", Analytical Biochemistry, 273(2):261-277.
Chaturvedi et al. (Jun. 2001) "Fucosylated Human Milk Oligosaccharides Vary Between Individuals and Over the Course of Lactation", Glycobiology, 11 (5):365-372.
Chaturvedi et al. (2001) "Survival of Human Milk Oligosaccharides in the Intestine of Infants", Advances in Experimental Medicine and Biology, 501:315-323.
Delmas et al. (1992) "Aminopeptidase N is a Major Receptor for the Entero-pathogenic Coronavirus TGEV", Nature, 357:417-420.
Hamosh M. (Feb. 2001) "Bioactive Factors in Human Milk", Pediatric Clinics of North America, 48(1):69-86.
Huang et al. (Jul. 2015) "Human Coronavirus HKU1 Spike Protein Uses O-Acetylated Sialic Acid as an Attachment Receptor Determinant and Employs Hemagglutinin-Esterase Protein as a Receptor-Destroying Enzyme", Journal of Virology, 89(14):7202-7213.
Krempl et al. (1995) "Analysis of Cellular Receptors for Human Coronavirus OC43", Advances in Experimental Medicine and Biology, 380:371-374.
Li et al. (Nov. 27, 2003) "Angiotensin-Converting Enzyme 2 is a Functional Receptor for the SARS Coronavirus", Nature, 426(6965):450-454.
Li et al. (2011) "Effects of ABO and FUT2 Genetic Transcription Absence on ABH histo-blood Group Antigen Expression in Lung Cancer Patients", Asian Pacific Journal of Cancer Prevention, 12(12):3201-3206.
Li et al. (Aug. 15, 2007) "Porcine Aminopeptidase N is a Functional Receptor for the PEDV Coronavirus", Virology, 365(1):166-172.
Liu et al. (Jun. 2015) "Receptor Usage and Cell Entry of Porcine Epidemic Diarrhea Coronavirus", Journal of Virology, 89(11):6121-6125.

(Continued)

*Primary Examiner* — Yih-Horng Shiao
(74) *Attorney, Agent, or Firm* — Mintz Levin Cohn Ferris Glovsky and Popeo, P.C.; Ingrid A. Beattie (57) ABSTRACT

The invention provides compositions and methods for utilizing oligosaccharides, such as isolated human milk oligosaccharides, to attenuate a respiratory pathogen infection and/or to promote recovery from a respiratory pathogen infection in the respiratory system and/or the GI tract of a subject.

11 Claims, 6 Drawing Sheets

(56) References Cited

OTHER PUBLICATIONS

Marcobal et al. (May 2010) "Consumption of Human Milk Oligosaccharides by Gut-Related Microbes", Journal of Agricultural and Food Chemistry, 58(9):5334-5340.
Martin-Sosa et al. (Jan. 2003) "Sialyloligosaccharides in Human and Bovine Milk and in Infant Formulas: Variations with the Progression of Lactation", Journal of Diary Science, 86(1):52-59.
Morrow et al. (Sep. 2004) "Human Milk Oligosaccharides are Associated with Protection Against Diarrhea in Breast-Fed Infants", The Journal of Pediatrics, 145(3):297-303.
Newburg David S. (Feb. 2001) "Bioactive Components of Human Milk: Evolution, Efficiency, and Protection", Advances in Experimental Medicine and Biology, 501(1):3-10.
Newburg et al. (Aug. 2005) "Human Milk Glycans Protect Infants Against Enteric Pathogens", Annual Review of Nutrition, 25:37-58.
Newburg David S. (Mar. 1999) "Human Milk Glycoconjugates that Inhibit Pathogens", Current Medicinal Chemistry, 6(2):117-127.
Newburg et al. (Mar. 1, 2004) "Innate Protection Conferred by Fucosylated Oligosaccharides of Human Milk Against Diarrhea in Breastfed Infants", Glycobiology, 14(3):253-263.
Newburg et al. (Jan. 2007) "Protection of the Neonate by the Innate Immune System of Developing Gut and of Human Milk", Pediatric Research, 61(1):2-8.
Newburg et al. (1998) "Role of Human-Milk Lactadherin in Protection Against Symptomatic Rotavirus Infection", The Lancet, 351(9110):1160-1164.
Ninonuevo et al. (Oct. 4, 2006) "A Strategy for Annotating the Human Milk Glycome", Journal of Agricultural and Food Chemistry, 54(20):7471-7480.
Parkkinen et al. (1987) "Isolation of Sialyl Oligosaccharides and Sialyl Oligosaccharide Phosphates from Bovine Colostrum and Human Urine", Methods in Enzymology, 138:289-300.
Prieto et al. (Jan. 24, 1997) "Expression of Human H-type a1,2-Fucosyltransferase Encoding for Blood Group H (O) Antigen in Chinese Hamster Ovary Cells. Evidence for Preferential Fucosylation and Truncation of Polylactosamine Sequences", The Journal of Biological Chemistry, 272(4):2089-2097.
Raj et al. (Mar. 14, 2013) "Dipeptidyl Peptidase 4 is a Functional Receptor for the Emerging Human Coronavirus-EMC", Nature, 495(7440):251-254.
Schultze et al. (Apr. 1992) "Bovine Coronavirus uses N-acetyl-9-O-acetylneuraminic Acid as a Receptor Determinant to Initiate the Infection of Cultured Cells", The Journal of General Virology, 73(Pt 4):901-906.
Schultze et al. (1993) "N-Acetylneuraminic Acid Plays a Critical Role for the Haemagglutinating Activity of Avian Infectious Bronchitis Virus and Porcine Transmissible Gastroenteritis Virus", Advances in Experimental Medicine and Biology, 342:305-310.
Schultze et al. (Aug. 1996) "Transmissible Gastroenteritis Coronavirus, but not the Related Porcine Respiratory Coronavirus, has a Sialic Acid (N-glycolylneuraminic Acid) Binding Activity", Journal of Virology, 70(8):5634-5637.
Shen et al. (Jul. 6, 2001) "Resolution of Structural Isomers of Sialylated Oligosaccharides by Capillary Electrophoresis", Journal of Chromatography A, 921(2):315-321.
Tresnan et al. (Dec. 1996) "Feline Aminopeptidase N Serves as a Receptor for Feline, Canine, Porcine, and Human Coronaviruses in Serogroup I", Journal of Virology, 70(12):8669-8674.
Walther et al. (Mar. 2013) "Glycomic Analysis of Human Respiratory tract Tissues and Correlation with Influenza Virus Infection", PLoS Palthogens, 9(3):e1003223 (16 pages).
Wilde et al. (2018) "Host Factors in Coronavirus Replication", Current Topics in Microbiology and Immunology, 419:1-42.
Williams et al. (Jul. 1, 1991) "Receptor for Mouse Hepatitis Virus is a Member of the Carcinoembryonic Antigen Family of Glycoproteins", Proceedings of the National Academy of Sciences, 88(13):5533-5536.
Wrapp et al. (Mar. 13, 2020) "Cryo-EM Structure of the 2019-nCoV Spike in the Prefusion Conformation", Science, 367(6483):1260-1263.
Wu et al. (Nov. 24, 2009) "Crystal Structure of NL63 Respiratory Coronavirus Receptor-binding Domain Complexed with its Human Receptor", Proceedings of the National Academy of Sciences, 106(47):19970-19974.
Yan et al. (Mar. 27, 2020) "Structural Basis for the Recognition of SARS-CoV-2 by Full-Length Human ACE2", Science, 367(6485):1444-1448.
Yang et al. (Aug. 26, 2014) "Receptor Usage and Cell Entry of Bat Coronavirus HKU4 Provide Insight into Bat-to-Human Transmission of MERS Coronavirus", Proceedings of the National Academy of Sciences, 111(34):12516-12521.
Yeager et al. (Jun. 4, 1992) "Human aminopeptidase N is a receptor for human coronavirus 229E", Nature, 357 (6377):420-422.
Zhao et al. (2020) "Relationship between the ABO Blood Group and the COVID-19 Susceptibility", medRxiv, 18 pages.
Zhou et al. (Mar. 2020) "A Pneumonia Outbreak Associated with a New Coronavirus of Probable Bat Origin", Nature, 579(7798):270-273.
Anand et al. (Sep. 2018) "Diet, Microbiota and Gut-Lung Connection", Frontiers in Microbiology, 9:2147 (12 pages).
Azzouz et al. (Jul. 2019) "Lupus Nephritis is Linked to Disease-Activity Associated Expansions and Immunity to a Gut Commensal", Annals of the Rheumatic Diseases, 78(7):947-956.
Bode Lars (Sep. 2012) "Human Milk Oligosaccharides: Every Baby Needs a Sugar Mama", Glycobiology, 22(9):1147-1162.
Bogiatzi et al. (2018) "Metabolic Products of the Intestinal Microbiome and Extremes of Atherosclerosis", Atherosclerosis, 273:91-97 (31 pages).
Brandsma et al. (Jan. 4, 2019) "A Proinflammatory Gut Microbiota Increases Systemic Inflammation and Accelerates Atherosclerosis", Circulation Research, 124(1):94-100.
Chen et al. (2018) "Inflammatory Responses and Inflammation-Associated Diseases in Organs", Oncotarget, 9(6):7204-7218.
Chen et al. (Mar. 3, 2020) "The SARS-CoV-2 Vaccine Pipeline: An Overview", Current Tropical Medicine Reports, 4 pages.
Chu et al. (Apr. 2, 2018) "Gut Microbiota in Multiple Sclerosis and Experimental Autoimmune Encephalomyelitis: Current Applications and Future Perspectives", Mediators of Inflammation, 2018:8168717 (17 pages).
Cummings et al. (2015) "DC-SIGN Binds 2-Fucosyl-Lactose (2FL) at Concentrations Available in Human Milk", The FASEB Journal, 29(1 Supplement): 890.10.
Grabinger et al. (Jun. 19, 2019) "Alleviation of Intestinal Inflammation by Oral Supplementation With 2-Fucosyllactose in Mice", Frontiers in Microbiology, 10:1385 (14 pages).
Guo et al. (2020) "The Origin, Transmission and Clinical Therapies on Coronavirus Disease 2019 (COVID-19) Outbreak—An Update on the Status", Military Medical Research, 7(1):11 (10 pages).
Hassan et al. (2020) "Coronavirus (COVID-19): A Review of Clinical Features, Diagnosis, and Treatment", Cureus, 12(3):e7355 (7 pages).
He et al. (Jan. 15, 2016) "Human Milk Components Modulate Toll-Like Receptor-Mediated Inflammation", Advances in Nutrition, 7(1):102-111.
He et al. (2016) "The Human Milk Oligosaccharide 2'-Fucosyllactose Modulates CD14 Expression in Human Enterocytes, thereby Attenuating LPS-lnduced Inflammation", Gut, 65(1):33-46.
Kasper Dennisl. (2009) "A Paradigm for Commensalism: The Role of a Specific Microbial Polysaccharide in Health and Disease", Nestle Nutrition Institute Workshop Series. Pediatric Program, 64:1-8; discussion 8-10, 251-257.
Kho et al. (Aug. 14, 2018) "The Human Gut Microbiome—A Potential Controller of Wellness and Disease", Frontiers in Microbiology, 9:1835 (23 pages).
Knip et al. (Sep. 23, 2017) "Modulation of Type 1 Diabetes Risk by the Intestinal Microbiome", Current Diabetes Reports, 17(11):105 (8 pages).
Koromyslova et al. (Aug. 2017) "Human Norovirus Inhibition by a Human Milk Oligosaccharide", Virology, 508:81-89.

(56) References Cited

OTHER PUBLICATIONS

Lee et al. (Jul. 2018) "Microbiome in the Gut-Skin Axis in Atopic Dermatitis", Allergy, Asthma & Immunology Research, 10(4):354-362.
Matthay et al. (Mar. 14, 2019) "Acute Respiratory Distress Syndrome", Nature Reviews. Disease Primers, 5(1):18 (22 pages).
Mazmanian et al. (May 29, 2008) "A Microbial Symbiosis Factor Prevents Intestinal Inflammatory Disease", Nature, 453(7195):620-625.
Ochoa-Repáraz et al. (Sep. 2010) "A Polysaccharide from the Human Commensal Bacteroides Fragilis Protects Against CNS Demyelinating Disease", Mucosal Immunology, 3(5):487-495.
Pickard et al. (Jun. 15, 2015) "Intestinal Fucose as a Mediator of Host-Microbe Symbiosis", Journal of Immunology, 194(12):5588-5593.
Rapozo et al. (Mar. 28, 2017) "Diet and Microbiota in Inflammatory Bowel Disease: The Gut in Disharmony", World Journal of Gastroenterology, 23(12):2124-2140.
Rogier et al. (Nov. 15, 2017) "Alteration of the Intestinal Microbiome Characterizes Preclinical Inflammatory Arthritis in Mice and its Modulation Attenuates Established Arthritis", Scientific Reports, 7(1):15613 (12 pages).
Ruiz-Palacios et al. (Apr. 18, 2003) "Campylobacter Jejuni binds Intestinal H(O) Antigen (Fuc alpha 1, 2Gal beta 1, 4GlcNAc), and Fucosyloligosaccharides of Human Milk Inhibit its Binding and Infection", Journal of Biological Chemistry, 278(16):14112-14120.
Sheahan et al. (Mar. 2020) "An Orally Bioavailable Broad-Spectrum Antiviral Inhibits SARS-CoV-2 and Multiple Endemic, Epidemic and Bat Coronavirus", bioRxiv, 34 pages.
Sodhi et al. (Feb. 2021) "The Human Milk Oligosaccharides 2'-Fucosyllactose and 6'-Sialyllactose Protect against the Development of Necrotizing Enterocolitis by Inhibiting Toll-like Receptor 4 Signaling", Pediatric Research, 89(1):91-101.
Stefka et al. (Sep. 9, 2014) "Commensal Bacteria Protect Against Food Allergen Sensitization", Proceedings of the National Academy of Sciences, 111(36):13145-13150.
Surana et al. (Jan. 2012) "The Yin Yang of Bacterial Polysaccharides: Lessons Learned from B. Fragilis PSA", Immunological Reviews, 245(1):13-26 (21 pages).
Thursby et al. (May 16, 2017) "Introduction to the Human Gut Microbiota", Biochemical Journal, 474(11):1823-1836.
Troy et al. (Jan. 2010) "Beneficial Effects of Bacteroides Fragilis Polysaccharides on the Immune System", Frontiers in Bioscience (Landmark Ed), 15:25-34.
Weichert et al. (Apr. 14, 2016) "Structural Basis for Norovirus Inhibition by Human Milk Oligosaccharides", Journal of Virology, 90(9):4843-4848.
Yu et al. (2012) "The Principal Fucosylated Oligosaccharides of Human Milk Exhibit Prebiotic Properties on Cultured Infant Microbiota", Glycobiology, 23(2):169-177.
Yu et al. (Nov. 2013) "Utilization of Major Fucosylated and Sialylated Human Milk Oligosaccharides by Isolated Human Gut Microbes", Glycobiology, 23(11):1281-1292.
Zehra et al. (Feb. 2018) "Human Milk Oligosaccharides Attenuate Antigen-Antibody Complex Induced Chemokine Release from Human Intestinal Epithelial Cell Lines", Journal of Food Science, 83(2):499-508.
Zhang et al. (Feb. 25, 2020) "The Cross-Talk Between Gut Microbiota and Lungs in Common Lung Diseases", Frontiers in Microbiology, 11:301 (14 pages).
Zhao et al. (Mar. 2019) "The Gut Microbiome in Food Allergy", Annals of Allergy, Asthma & Immunology, 122(3):276-282.
Zheng et al. (Oct. 2018) "Gut Microbiome in type 1 Diabetes: A Comprehensive Review", Diabetes/Metabolism Research and Reviews, 34(7):e3043 (9 pages).

\* cited by examiner

FUCOSYLATED OLIGOSACCHARIDES FOR PREVENTION OF CORONAVIRUS INFECTION

RELATED APPLICATIONS

This application claims the benefit of U.S. Ser. No. 63/024,464 filed May 13, 2020, which is incorporated herein by reference in its entirety.

FIELD OF THE INVENTION

The invention provides compositions and methods for utilizing fucosylated oligosaccharides to attenuate or prevent a pathogenic virus infection to a subject.

BACKGROUND OF THE INVENTION

The recent pandemic of COVID-19 infection to millions of people worldwide presents an urgent need for a treatment capable of preventing or attenuating coronavirus infection.

SUMMARY OF THE INVENTION

Some coronaviruses, such as SARS-CoV-2 (COVID-19), are known to bind to the angiotensin-converting enzyme 2 (ACE2) receptor, which has many glycosylation sites, of an animal subject. The invention is based on the discovery that infections with tested strains of coronaviruses were increased in individuals with histo-blood group types (e.g., the ABO blood group types) that involve fucosylation, and that host fucosyltransferase 2 (FUT2) secretor status is relevant to endemic coronavirus infections. Infection of SARS-CoV-2 and other major respiratory pathogens can be reduced by administration of fucosylated oligosaccharides [such as human milk glycans or human milk oligosaccharides (hMOS) described herein], via inhalation, pulmonary lavage, oral ingestion, and/or injection. These oligosaccharides function as competitive inhibitors of host receptor binding by the virus, thereby reducing risk of symptomatic infection. The compositions described herein, such as fucosylated human milk oligosaccharides [e.g., 2' fucosyllactose (2' FL), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), and Lacto-N-difucohexaose II (LDFH II), etc.], are indigestible or partially indigestible (by the host), but provide health benefits to the host by at least one of multiple mechanisms, such as attenuating the binding of respiratory pathogens, such as coronaviruses, to its receptor in the respiratory system (e.g., lung and bronchi) and/or the GI tract of a subject, thus attenuating or inhibiting viral infection. In addition, the invention provides methods of using such compositions comprising at least one isolated fucosylation oligosaccharide, such as at least one isolated human milk oligosaccharide (HMO), in an amount effective to prevent, attenuate/reduce, and/or inhibit a respiratory pathogen (such as a coronavirus) infection and/or to promote recovery from a respiratory pathogen infection in the respiratory system (e.g., lung and bronchi) and/or the gastrointestinal (GI) tract of a subject. Preferably, the oligosaccharide comprises at least one isolated HMO comprising 2'-fucosyllactose (2'-FL), 3-fucosyllactose (3-FL), lactodifucotetraose (LDFT), other HMOS described herein, or combinations thereof.

TABLE 1

| HMOS names and structures | | |
|---|---|---|
| 2'-FL | 2'-Fucosyllactose | Fucα1,2Galβ1,4Glc |
| 3-FL | 3-Fucosyllactose | Galβ1,4→Glc; Fucα1,3↗ |
| 3'-FL | 3'-galactosyllactose | Galβ1,3Galβ1,4Glc |
| 4'-FL | 4'-galactosyllactose | Galβ1,4Galβ1,4Glc |
| 6'-FL | 6'-galactosyllactose | Galβ1,6Galβ1,4Glc |
| LDFT | Lactodifucotetraose | Fucα1,2Galβ1,4→Glc; Fucα1,3↗ |
| LNT | Lacto-N-tetraose | Galβ1,3GlcNAcβ1,3Galβ1,4Glc |
| LNnT | Lacto-N-neotetaose | Galβ1,4GlcNAcβ1,3Galβ1,4Glc |
| LNF-I | Lacto-N-fucopentaose I | Fucα1,2Galβ1,3GlcNAcβ1,3Galβ1,4Glc |
| LNF-II | Lacto-N-fucopentaose II | Galβ1,3→GlcNAcβ1,3Galβ1,4Glc; Fucα1,4↗ |
| LNF-III | Lacto-N-fucopentaose III | Galβ1,4→GlcNAcβ1,3Galβ1,4Glc; Fucα1,3↗ |
| LDFH-I | Lacto-N-difucohexaose I | Fucα1,2Galβ1,3→GlcNAcβ1,3Galβ1,4Glc; Fucα1,4↗ |
| LDFH-II | Lacto-N-difucohexaose II | Galβ1,3→GlcNAcβ1,3Galβ1,4Glc; Fucα1,4↗ Fucα1,3↗ |
| 3'-SL | 3'-Sialyllactose | NANAα2,3Galβ1,4Glc |
| 6'-SL | 6'-Sialyllactose | NANAα2,6Galβ1,4Glc |
| DSLNT | Disialylloacto-N-tetraose | NANAα2,3Galβ1,3GlcNAcβ1,3Galβ1,4Glc; NANAα2,6↗ |

The compositions of the invention are administered alone or, alternatively, in conjunction with other agents for preventing, attenuating and/or treating a respiratory pathogen infection. The compositions optionally include a pharmaceutically-acceptable excipient or inactive ingredients.

In one aspect, the invention provides a composition comprising at least one isolated human milk oligosaccharide (HMO) in an amount effective to prevent, reduce, and/or inhibit a respiratory pathogen (e.g., a virus) from binding to an animal cell or tissue. In some embodiments, the at least one isolated human milk oligosaccharide (HMO) comprises 2'-fucosyllactose (2'-FL), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), or Lacto-N- difucohexaose II (LDFH II). In some embodiments, the composition is in the form of a powder, a tablet, an aerosol, feed for mammalian animals, a packet of sugar, yogurt, a beverage, a weaning food, or an infant formula. In some embodiments, the respiratory pathogen is a virus. For example, the virus may comprise i) a coronavirus; ii) a severe acute respiratory syndrome virus (SARS-CoV); iii) a SARS-CoV-2 (COVID-19) virus; and/or iv) a hCoV-NL63. In some embodiments, the virus binds to the ACE2 receptor on the animal cell or tissue. In some embodiments, the binding between the virus and the animal cell or tissue is mediated by fucosylation on the animal cell or tissue, such as at least one fucosylated oligosaccharide or one fucosylated polypeptide or protein. In some embodiments, the animal cell or tissue described herein comprises a tissue of an animal respiratory system (e.g., lung and bronchi) or the gastrointestinal (GI) tract mucosa or a cell in such tissue. For example, an animal respiratory tissue may include a tissue from at least one of the lung or the upper respiratory tract (including, e.g., nose, nasal cavities, sinuses, pharynx and the part of the larynx above the vocal folds) or the lower tract (including, e.g., the lower part of the larynx, the trachea, bronchi, bronchioles and the alveoli).

In some embodiments, the animal cell or tissue described herein expresses a fucosyltransferase 2 (FUT2) genotype.

In some embodiments, the animal is a human, non-human primate, mouse, rat, dog, cat, horse, cattle, sheep, pig, chicken, or goat.

In another aspect, the invention provides a use of the composition described herein to prevent, reduce, or inhibit an infection of a respiratory pathogen (e.g., a virus) in a subject, wherein the respiratory pathogen (e.g., the virus) binds to a cell or tissue in the subject. In some embodiments, the composition prevent, reduce, or inhibit the binding of the respiratory pathogen (e.g., the virus) to the cell or tissue in the subject. In some embodiments, the subject expresses a fucosyltransferase 2 (FUT2) genotype. In some embodiments, the subject is a human, non-human primate, mouse, rat, dog, cat, horse, cattle, sheep, pig, chicken, or goat.

In another aspect, the invention provides a method of preventing, attenuating, or treating a respiratory pathogen (e.g., a virus) infection and/or promoting recovery from a respiratory pathogen (e.g., a virus) infection in a subject, comprising administering to the subject a pharmaceutically effective amount of at least one isolated human milk oligosaccharide (HMO). In some embodiments, the at least one isolated human milk oligosaccharide (HMO) comprises 2'-fucosyllactose (2'-FL), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), or Lacto-N-difucohexaose II (LDFH II). The some embodiments, the respiratory pathogen (e.g., the virus) comprises i) a coronavirus; ii) a severe acute respiratory syndrome virus (SARS-CoV); iii) a SARS-CoV-2 (COVID-19) virus; and/or iv) a hCoV-NL63. In some embodiments, the respiratory pathogen (e.g., the virus) binds to the ACE2 receptor on a cell or tissue of the subject. In some embodiments, the at least one isolated HMO competes with the virus for binding to the ACE2 receptor on a cell or tissue of the subject. In some embodiments, the binding between the respiratory pathogen (e.g., the virus) and the cell or tissue of the subject is mediated by fucosylation (e.g., fucosylation to a glycan, an oligosaccharide, and/or a polypeptide or protein). In some embodiments, the cell or tissue to which respiratory pathogen (e.g., the virus) binds to comprises a tissue of the respiratory system (e.g., lung and bronchi) or a gastrointestinal (GI) tract mucosa or a cell in such tissue of the subject. For example, a respiratory tissue may include a tissue from at least one of the lung or the upper respiratory tract (including, e.g., nose, nasal cavities, sinuses, pharynx and the part of the larynx above the vocal folds) or the lower tract (including, e.g., the lower part of the larynx, the trachea, bronchi, bronchioles and the alveoli) of the subject. In some embodiments, the subject described herein is a human, non-human primate, mouse, rat, dog, cat, horse, cattle, sheep, pig, chicken, or goat. In some embodiments, the subject expresses a fucosyltransferase 2 (FUT2) genotype. In some embodiments, the subject has type A, type B, type AB, or type O of the ABO blood group. In some embodiments, the subject has an ABO blood group type A, B, or AB. In some embodiments, the at least one isolated HMO described herein is administered to the respiratory system (e.g., lung and bronchi) or the gastrointestinal (GI) tract mucosa of the subject. In some embodiments, the at least one isolated HMO described herein is administered to the subject through an acceptable routes, such as inhalation, pulmonary lavage, oral ingestion, anal administration, and/or injection. In some embodiments, the pharmaceutically effective amount for the at least one isolated HMO described herein is equivalent to a dosage of i) about 0.2 g to 20 g per day; ii) about 1 g to 10 g per day; and/or ii) about 5 g to 10 g per day. In some embodiments, the pharmaceutically effective amount for the at least one isolated HMO described herein is equivalent to a dosage of about 0.01 g to about 20 g per day, about 0.01 g to about 10 g per day, about 0.1 g to about 10 g per day, about 1 g to about 10 g per day, about 1 g to about 5 g per day, about 5 g to about 10 g per day, or any dosages found effective to the specific subject.

As used herein, an "isolated" or "purified" oligosaccharide is substantially free of other oligosaccharides, with which it naturally occurs in human milk. Purified oligosaccharides are also free of cellular material when produced biosynthetically, or other chemicals when chemically synthesized. Purified compounds are at least 50% or 60% (by dry weight) of the compound of interest. Preferably, the preparation is at least 70%, 75%, 80%, 85%, 90%, 95%, 98%, 99%, or more, pure, by weight the compound of interest. For example, a purified oligosaccharide, e.g., 2'-FL, 3-FL, LDFT, or others described herein, is one that is at least 50%, 60%, 70%, 75%, 80%, 85%, 90%, 91%, 92%, 93%, 94%, 95%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The oligosaccharides are purified and used in a number of products for consumption by humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

Similarly, by "substantially pure" is meant an oligosaccharide that has been separated from the components that naturally accompany it. Typically, the oligosaccharide is substantially pure when it is at least 50%, 60%, 70%, 75%, 80%, 85%, 90%, 95%, 99%, or even more, by weight, free from the proteins and naturally-occurring organic molecules with which it is naturally associated.

The mean concentrations of 2'-FL, 3-FL, and LDFT in human milk are as follows: 2'-FL=2.43 g/L (±0.26), 3-FL=0.86 g/L (±0.10), and LDFT=0.43 g/L (±0.04; Chaturvedi P, et al. 2001 Glycobiology, May; 11(5):365-72).

Thus, the mean ratio of 2'-FL:3FL:LDFT in human milk is 5.65:2:1. To form compositions comprising more than one isolated oligosaccharide, e.g., a composition comprising two isolated oligosaccharides, the first oligosaccharide (e.g., 2'-FL, 3-FL, or LDFT) and the second oligosaccharide may be mixed in any ratio described herein. In some embodiments, the composition comprises the first purified oligosaccharide (e.g., 2'-FL, 3-FL, or LDFT) and the second oligosaccharide in a ratio of, e.g., 1:1, 1:2, 1:5, 1:10, 1:100, 100:1, 10:1, 5:1, or 2:1, or any other ratio suitable to obtain prebiotic effects.

In some embodiments, the subject is pre-treated with at least one agent for preventing the respiratory pathogen infection (e.g., an antibiotic). Such antibiotics may include, for example, at least one of Kanamycin, Gentamicin, Colistin, Metronidazole, Vancomycin, or any such agents or antibiotics known by a skilled artisan with such function.

In some embodiments, the at least one isolated HMO attenuates the respiratory pathogen infection, measurable by, e.g., pathogen colonization and/or adhesiveness, to cells or tissue of the subject. In some embodiments, the at least one isolated HMO attenuates the pathogen infection, e.g., the pathogen colonization and/or adhesiveness to cells or tissue of the subject by at least 20%, 30%, 40%, 50%, 60%, 65%, 70%, 75%, 80%, 85%, 90%, 95%, or more.

The at least one isolated HMO described herein may comprise 2'-FL, 3-FL, 6'-SL, 3'-SL, LNFPI, TFiLNO, or other oligosaccharides. In some embodiments, the at least one isolated HMO comprises 2'-FL. In some embodiments, the at least one isolated HMO is at least 50%, 60%, 70%, 80%, 90%, 95%, 99%, or more pure (in, e.g., w/w).

In some embodiments, the concentration by weight of the at least one isolated HMO in the composition is i) from about 1% to about 99%; ii) from about 10% to about 90%; iii) from about 30% to about 70%; iv) from about 40% to about 60%; or v) about 50%.

In some embodiments, the composition described herein may include a $2^{nd}$, $3^{rd}$, $4^{th}$, $5^{th}$, $6^{th}$, $7^{th}$, $8^{th}$, $9^{th}$, or $10^{th}$ purified oligosaccharide (concentration by weight as described above).

In some embodiments, the composition described herein comprises between 0.01 g and 10 g of the first purified oligosaccharide, e.g., 2'-FL, 3-FL, LDFT, or others described herein, per 10 grams of composition. For example, the composition comprises between 0.1 g and 5 g, between 0.5 g and 5 g, between 1 g and 5 g, or between 1.5 g and 3 g of the at least one isolated oligosaccharide, e.g., 2'-FL, 3-FL, LDFT, or others described herein, per 10 grams of composition. In some embodiments, the composition comprises between 0.01 g and 1 g of the at least one isolated oligosaccharide per gram of composition. In some embodiments, the composition comprises between 0.01 g 2'-FL and 1 g 2'-FL per gram of composition.

In some embodiments, the composition described herein comprises a second oligosaccharide, in addition to the at least one isolated oligosaccharide in the composition. In some embodiments, the second oligosaccharide is a purified human milk oligosaccharide. In some embodiments, the second oligosaccharide is not a human milk oligosaccharide. In some embodiments, the second oligosaccharide comprises fructo-oligosaccharides (FOS), galacto-oligosaccharides (GOS), or lactulose. In some embodiments, the second oligosaccharide comprises galacto-oligosaccharides (GOS).

The subject described herein may be a mammal. In some embodiments, the subject is a human. In some embodiments, the subject is a non-human mammal. In some embodiments, the subject is a pre-term infant, a term infant, a child, an adolescent, or an elder.

The composition described herein is in the form of a tablet, a capsule, a powder, a beverage, or an infant formula. For example, the at least one isolated oligosaccharide (such as HMO) of the invention are in the form of powdered/dry milk. By "infant" is meant a child under the age of 12 months. By "infant formula" is meant a foodstuff intended for particular nutritional use by infants aged under twelve months and constituting the principal liquid element in the progressively diversified diet of this category of person. In some embodiments, the composition described herein is provided in dry milk, in mashed rice, in a banana, in a porridge, or in a gruel. Due to the surge in disease in infants at weaning, the HMOS of the invention are added to weaning foods (e.g., mashed rice, bananas, porridges and other gruels, formula, etc.) to reduce or ameliorate these diseases. Optionally, the HMOS described herein are added to the weaning foods during the manufacturing process. Alternatively, the HMOS are added to the weaning foods after the manufacturing process, but prior to ingestion. For example, packets of sugars including one or more isolated or purified HMOS are added to weaning foods prior to infant ingestion.

The composition described herein may be also added to other consumable products such as yogurt or probiotic beverages for consumption by infants, children, and adults. For example, the composition may be added to powdered/dry milk.

The composition described herein may be administered to the subject locally or systemically through other viable routes to the respiratory system or the GI tract.

Administration of the composition for use in the method improves the overall health of the respiratory system and/or the gastrointestinal tract by influencing many members of the microbial community. The composition for use in the method described herein may inhibit pathogen binding to cell or mucosal surfaces, and attenuate pathogen infection. For example, administration of the composition of the invention results in an improvement of at least one symptom related to the pathogen infection, such as cough, shortness of breath or difficulty breathing, fever, chills, repeated shaking with chills, muscle pain, headache, sore throat, new loss of taste or smell, etc. Children have similar symptoms to adults and generally have mild illness. In some embodiments, the subject described herein has at least one symptom of diseases and disorders associated with the pathogen infection or rendering the subject vulnerable to the pathogen infection, selected from the group consisting of respiratory tract infection, ear, nose, or throat (ENT) infection, or an infectious complication in surgical and critically ill patients. In one example, the subject is a mammal in need of treatment, e.g., a subject that has been diagnosed with infections or infection related to the pathogen infection, such as respiratory tract infection, ear, nose, or throat (ENT) infection, or an infectious complication in surgical and critically ill patients.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a sufficient amount of the formulation or component to provide the desired effect. For example, by "an effective amount" is meant an amount of an oligosaccharide to prevent, attenuate, and/or inhibit, a respiratory pathogen binding to, and thus infection of, a cell or tissue of a subject, or to treat a respiratory pathogen infection in a subject. Ultimately, the attending physician or veterinarian decides the appropriate amount and dosage regimen.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIGS. 2A and 2B are a series of charts showing exemplary MALDI-TOF mass spectra of permethylated N-glycans of human lung and bronchus. The FUT2 gene regulates expression of both H antigen (directly) and A/B blood group antigens (indirectly). Specifically, ABO N-glycan profiles on the surface of human lung (FIG. 2A) or human bronchus (FIG. 2B) were obtained from the 50% MeCN fraction from a C18 Sep-Pak column. Annotated structures are according to the Consortium for Functional Glycomics guidelines. All molecular ions are [M+Na]+. Structures are based on composition, tandem MS, and the biosynthetic knowledge. Due to the presence of heterogeneous multiantennary structures with extended LacNAc repeats, the annotations are simplified throughout by using biantennary structures with the extensions listed in parentheses.

FIG. 4A is a linear chart and an image of Western Blot, showing a representative size exclusion chromatography purification profile of full-length human ACE2 in complex with B(0)AT1. mAU refers to milli-absorbance units; MWM refers to molecular weight marker. FIG. 4B is an image showing a 3-D cryo-EM map of the ACE2-B(0)AT1 complex. Protomer A of ACE2 (upper right), protomer B of ACE2 (upper left), protomer A of B(0)AT1 (lower right) and protomer B of B(0)AT1 (lower left) are shown. FIG. 4C is a cartoon representation of the atomic model of the ACE2-B(0)AT1 complex. The glycosylation moieties are shown as sticks. The complex shows the PD (upper right) and CLD (middle right) subunits in one ACE2 protomer. FIG. 4D is a cartoon representation of an open conformation of the ACE2-B(0)AT1 complex. The two PDs, which contact each other in the closed conformation, are separate in the open conformation.

DETAILED DESCRIPTION

Some respiratory pathogens, such as coronaviruses, infect millions of people and cause enormous mobility and mortality. The health of individuals, especially their respiratory system and the GI tract vulnerable for pathogen infection, depending on host age, disease, microorganism infection, stress, nutritional components, and pharmaceutical treatments.

Described herein are compositions that contain at least one fucosylated oligosaccharide, such as at least one isolated human milk oligosaccharide (HMO), in an amount effective to prevent, attenuate/reduece, and/or inhibit a respiratory pathogen infection and/or to promote recovery from the pathogen infection in the respiratory system and/or the GI tract of a subject. Such fucosylated oligosaccharides include, e.g., 2'-fucosyllactose (2'-FL), 3-fucosyllactose (3-FL), lactodifucotetraose (LDFT), and others described herein. The compositions described herein prevent, attenuate, and/or inhibit the binding, and thus the entry for infection, of the pathogen to a cell or tissue of the respiratory system and/or the GI tract of the subject. Not intended to be limiting, the binding and/or the infection require fucosylation on the cell or tissue, while the compositions described herein compete with endogenous receptors for the pathogen to bind the pathogen, thus preventing, attenuating or inhibiting the pathogen from binding to the cell or tissue and causing infection.

As described in details below, at least one isolated human milk oligosaccharide (HMO) is administrated in an amount effective to prevent, attenuate or inhibit a respiratory pathogen (e.g., a coronavirus) infection and/or to promote recovery from a respiratory pathogen infection in the respiratory system and/or the gastrointestinal (GI) tract of a subject. For example, as described in detail below, at least one isolated and/or purified 2'-FL, 3-FL, LDFT, or other HMOs, is administered to selectively prevent, attenuate or inhibit binding of the pathogen to its receptor in the respiratory system and/or the GI tract of the subject, thus preventing, attenuating or inhibiting the pathogen infection.

Respiratory Pathogens

Multiple pathogens may infect the respiratory system and/or the GI tract of a subject described herein. For example, many coronaviruses, such as those in Table 5, including at least SARS-CoV, SARS-CoV-2, and hCoV-NL63, are known respiratory pathogens.

Coronaviruses are a group of related RNA viruses that cause diseases in mammals and birds. In humans, these viruses cause respiratory tract infections that can range from mild to lethal. Mild illnesses include some cases of the common cold (which is caused also by certain other viruses, predominantly rhinoviruses), while more lethal varieties can cause SARS, MERS, and COVID-19. Symptoms in other species vary: in chickens, they cause an upper respiratory tract disease, while in cows and pigs they cause diarrhea.

Severe acute respiratory syndrome-coronavirus 2 (SARS-CoV-2) is a positive strand RNA virus that causes severe respiratory syndrome in humans. The resulting outbreak of coronavirus disease 2019 (COVID-19) has emerged as a severe epidemic worldwide. The genome of SARS-CoV-2 shares about 80% identity with that of SARS-CoV and is about 96% identical to the bat coronavirus BatCoV RaTG13 (Zhou et al., (2020) A pneumonia outbreak associated with a new coronavirus of probable bat origin. *Nature* 579:270-273).

According to CDC, people with COVID-19 have had a wide range of symptoms reported—ranging from mild symptoms to severe illness. Symptoms may appear 2-14 days after exposure to the virus. People having COVID-19 infection may have cough, shortness of breath or difficulty breathing, or at least two of these symptoms: fever, chills, repeated shaking with chills, muscle pain, headache, sore throat, new loss of taste or smell, etc. Children have similar symptoms to adults and generally have mild illness.

In the case of SARS-CoV, the spike glycoprotein (S protein) on the virion surface mediates receptor recognition and membrane fusion. During viral infection, the trimeric S protein is cleaved into S1 and S2 subunits and S1 subunits are released in the transition to the post-fusion conformation. S1 contains the receptor binding domain (RBD), which directly binds to the peptidase domain (PD) of angiotensin-converting enzyme 2 (ACE2), whereas S2 is responsible for membrane fusion. When S1 binds to the host receptor ACE2, another cleavage site on S2 is exposed and is cleaved by host proteases, a process that is critical for viral infection. A recent publication reported the structure of the S protein of SARSCoV-2 and showed that the ectodomain of the SARS-CoV-2 S protein binds to the PD of ACE2 with a dissociation constant (Kd) of ~15 nM [Wrapp et al., (2020) Science eabb2507].

ABO Blood Groups

The ABO blood group system is used to denote the presence of one, both, or neither of the A and B antigens on erythrocytes. In human blood transfusions it is the most important of the 36 different blood type (or group) classification systems currently recognized. A detailed description is shown in FIG. 1. Blood containing red cells with type A antigen on their surface has in its serum antibodies against type B red cells. If, in transfusion, type B blood is injected into persons with type A blood, the red cells in the injected blood will be destroyed by the antibodies in the recipient's blood. In the same way, type A red cells will be destroyed by anti-A antibodies in type B blood. Type O blood can be injected into persons with type A, B, or O blood unless there is incompatibility with respect to some other blood group system also present. Persons with type AB blood can receive type A, B, or O blood.

The O antigen, eponymous for the O blood group type, is a glycan moiety with an α-1,2 linked fucose, also known as the H antigen when expressed in exocrine secretions. In the A blood group type, this motif is masked by an N-acetylgalactosamine, creating steric hindrance that inhibits binding by O antibodies or ligands. Similarly, in the B blood group type, the O antigen is masked by galactose. For the AB blood group type, the O antigen is masked by both, providing the strongest inhibition of binding by O ligands (Prieto et al. (1997) Expression of human H-type alpha1,2-fucosyltransferase encoding for blood group H(O) antigen in Chinese hamster ovary cells. Evidence for preferential fucosylation and truncation of polylactosamine sequences. *J Biol Chem* 272, 2089-2097).

Human Milk Glycans or Human Milk Oligosaccharides (HMOs)

Human milk contains a diverse and abundant set of neutral and acidic oligosaccharides. For example, the purified HMO described herein, such as fucosylated oligosaccharides, e.g., 2'-fucosyllactose (2'-FL), 3-fucosyllactose (3-FL), and lactodifucotetraose (LDFT), are typically found in human milk. Human milk oligosaccharides as a class survive transit through the intestine of infants very efficiently, being essentially indigestible (Chaturvedi, P et al. 2001 Adv Exp Med Biol, 501:315-323). Although these molecules may not be utilized directly by infants for nutrition, they nevertheless serve critical roles in the establishment of a healthy gut microbiome (Marcobal A, et al. 2010 J Agric Food Chem, 58:5334-5340), in the prevention of disease (Newburg D, et al. 2005 Annu Rev Nutr, 25:37-58), and in immune function (Newburg and Walker (2007) Protection of the neonate by the innate immune system of developing gut and of human milk. *Pediatr Res* 61, 2-8). Despite millions of years of exposure to human milk oligosaccharides (HMOS), pathogens have yet to develop ways to circumvent the ability of HMOS to prevent adhesion to target cells and to inhibit infection. The ability to utilize HMOS as pathogen adherence inhibitors promises to address the current crisis of burgeoning antibiotic resistance. Human milk oligosaccharides represent the lead compounds of a novel class of therapeutics against some of the most intractable scourges of society.

Human milk glycans, which comprise both unbound oligosaccharides and their glycolconjugates, play a significant role in the protection and development of infant organs, such as the gastrointestinal (GI) tract. Milk oligosaccharides found in various mammals differ greatly, and composition in humans is unique (Hamosh M, 2001 Pediatr Clin North Am, 48:69-86; Newburg D, 2001 Adv Exp Med Biol, 501:3-10). Moreover, glycan levels in human milk change throughout lactation and also vary widely among individuals (Morrow A et al., 2004 J Pediatr, 145:297-303; Chaturvedi P et al., 2001 Glycobiology, 11:365-372). Approximately 200 distinct human milk oligosaccharides have been identified and combinations of simple epitopes are responsible for this diversity (Newburg D, 1999 Curr Med Chem, 6:117-127; Ninonuevo M et al., 2006 J Agric Food Chem, 54:7471-74801). Human milk oligosaccharides are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). Human milk oligosaccharides are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J, et al. 1999 Anal Biochem, 273:261-277; Martin-Sosa, et al. 2003 J Dairy Sci, 86:52-59; Parkkinen J and Finne J, 1987 Methods Enzymol, 138:289-300; Shen Z, et al. 2001 J Chromatogr A, 921:315-321). Approximately 70-80% of oligosaccharides in human milk, e.g., 2'-fucosyllactose (2'-FL) and 3-fucosyllactose (3-FL), lactodifucotetraose (LDFT), are fucosylated.

Human milk glycans have structural homology to cell receptors for enteropathogens and function as receptor decoys. For example, respiratory pathogens, such as coronaviruses, bind specifically to the ACE2 receptor. Coronavirus binding and infectivity may thus be inhibited by 2'-FL and other glycans. Similarly, some diarrheagenic *E. coli* pathogens are strongly inhibited in vivo by human milk oligosaccharides containing 2-linked fucose moieties. Several major strains of human caliciviruses, especially the noroviruses, also bind to 2-linked fucosylated glycans, and this binding is inhibited by human milk 2-linked fucosylated glycans. Consumption of human milk that has high levels of these 2-linked fucosyloligosaccharides was associated with lower risk of norovirus, *Campylobacter*, ST of *E. coli*-associated diarrhea, and moderate-to-severe diarrhea of all causes in a Mexican cohort of breastfeeding children (Newburg D et al., 2004 Glycobiology, 14:253-263; Newburg D et al., 1998 Lancet, 351:1160-1164).

Human Milk Glycans or Human Milk Oligosaccharides (HMOs) to Attenuate a Respiratory Pathogen Infection and/or to Promote Recovery from a Respiratory Pathogen Infection Human milk contains a complex oligosaccharide mixture attenuating a respiratory pathogen (e.g., a coronavirus) infection and/or promoting recovery from a respiratory pathogen infection. As described herein, human milk oligosaccharides such as 2'-fucosyllactose (2'-FL, MW=488), 3-fucosyllactose (3-FL, MW=488), and lactodifucotetraose (LDFT, MW=635) have such properties and are administered, as described herein, to prevent, attenuate, inhibit, and/or treat a respiratory pathogen (e.g., a coronavirus) infection and/or to promote recovery from a respiratory pathogen (e.g., a coronavirus) infection. Such oligosaccharides are short-chain carbohydrates with a degree of polymerization between 2 and 60, and are indigestible by human or animal digestive systems.

As described herein, human milk glycans or HMOS function as agents that prevent, attenuate, and/or inhibit the respiratory pathogen (e.g., a coronavirus) from binding (thus affecting the pathogen colonization and/or adhesiveness) to its natural receptor in the respiratory system or the GI tract of a subject. The glycans or HMOS described herein are not limited to use in human infants or adults. They may also be administered to an infant or adult mammal. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. Preferably, the mammal is a human.

The invention also provides using other HMOS or glycans, or other agents, in addition to at least one HMO or glycan, for attenuating the pathogen infection. Such additional agents may include, e.g., fructo-oligosaccharides (FOS) and galacto-oligosaccharides (GOS).

Pharmaceutically available and/or effective administration routes may be used to deliver the fucosylated oligosaccharides (such as HMOS) described herein to a subject. With no intention to be limiting, the fucosylated oligosaccharides may be administered locally or systemically to a subject, including administering to, e.g., the respiratory system and/or the GI tract of the subject, via, e.g., inhalation, pulmonary lavage, oral ingestion, anal administration, infusion, and/or injection. Administration routes also include, but not limited to, administering to a subject intravenously, intradermally, intraperitoneally, intrapleurally, intratracheally, intramuscularly, subcutaneously, by injection, and by infusion.

Dosages and dosing regimes may be determined by a doctor or a medical personnel accordingly to each patient's individual situation. Generally, HMOS, such as 2'-FL, can be given orally at about 1-20 g/day to reduce infection of the lung. Oral HMOS, such as 2'-FL, may be administered either by itself in tablet or powder form, or it may be conveniently dissolved in a little water or another beverage, or it may be included in foodstuffs or in food or medical supplements. The preferred adult dose is generally equivalent to about 10 g per day, but anywhere between about 0.2 g per day up to about 20 g per day may be taken. For example, potential dosages may include about 0.01 g to about 20 g per day, about 0.01 g to about 10 g per day, about 0.1 g to about 10 g per day, about 1 g to about 10 g per day, about 1 g to about 5 g per day, about 5 g to about 10 g per day, or any dosages found effective to the subject. Specifically, 2'-FL is a natural component of human milk and as such it is non-toxic, however high doses (i.e. >10 g per day) may lead to mild gut discomfort and a reversible osmotic diarrhea.

Example 1: A Correlation Between Virus Infection and Cell Surface Oligosaccharide Components of the ABO Blood Group Types Early in the COVID-19 pandemic, Zhao et al (2020) conducted a case-control study of COVID-19 hospitalization in two regions of China: Wuhan & Shenzhen, indicates that SARS-CoV-2 hospitalization rates differ by ABO blood group type (see Zhao et al. (2020) Relationship between the ABO Histo-Blood Group and the COVID-19 Susceptibility. medRxiv 2020.03.11.20031096; doi: https://doi.org/10.1101/2020.03.11.20031096). In each region, hospitalized patients' ABO blood group type was compared to blood group typing data. A summary of parts of their results is given in the Table 2 below.

TABLE 2

SARS-CoV-2 hospitalizations by ABO blood groups in China

| Study Groups | Total no. | Number (Percentage) of individuals by blood group type | | | | |
|---|---|---|---|---|---|---|
| | | A | B | AB | All non-O | O (referenced) |
| Wuhan COVID-19 patients (from 2 hospitals) | 1775 | 670 (37.8%) | 469 (26.4%) | 178 (10.0%) | 1317 (74.2%) | 458 (25.8%) |
| Wuhan regional controls | 3694 | 1188 (32.2%) | 920 (24.9%) | 336 (9.1%) | 2444 (66.2%) | 1250 (33.8%) |
| Odds ratio (95% CI) | | 1.54 (1.3, 1.8) | 1.39 (1.2, 1.6) | 1.45 (1.2, 1.8) | 1.47 (1.3, 1.7) | 1.0 (N/A) |
| p-value | | <0.0001 | <0.0001 | 0.0006 | <0.0001 | N/A |

TABLE 2-continued

SARS-CoV-2 hospitalizations by ABO blood groups in China

| Study Groups | Total no. | A | B | AB | All non-O | O (referenced) |
|---|---|---|---|---|---|---|
| Shenzhen COVID-19 patients | 285 | 82 (28.8%) | 83 (29.1%) | 39 (13.7%) | 204 (71.6%) | 81 (28.4%) |
| Shenzhen regional controls | 23386 | 6728 (28.8%) | 5880 (25.1%) | 1712 (7.3%) | 14320 (61.2%) | 9066 (38.8%) |
| Odds ratio (95% CI) | | 1.36 (1.0, 1.9) | 1.58 (1.1, 2.2) | 2.55 (1.7, 3.8) | 1.59 (1.2, 2.1) | 1.0 |
| p-value | | 0.048 | 0.003 | <0.0001 | <0.0001 | N/A |

Zhao et al emphasized a small reported association with A blood group—1.2 fold increased risk. However, their data analysis and conclusions are flawed. A re-analysis of Zhao's data described here led to a different conclusion. For example, Zhao et al stated that their results showed that blood group A was associated with a higher risk for acquiring COVID-19 compared with non-A blood groups, whereas blood group O was associated with a lower risk for the infection compared with non-O blood groups. However, the error of their analytic approach is that they compared each blood group type to all others. This approach obscured the observation that there is no statistical difference across A, B, and AB blood group types; all were significantly and similarly elevated vs O blood group type. A blood group should not be singled out.

Thus, the re-analysis found that only O blood group type differed from the others, and was consistently protective, and the non-O blood groups odds of COVID-19 hospitalization was increased by about 1.5-fold, which is of public health significance.

SARS-CoV-2 shares ~80% amino acid sequence homology with SARS-CoV spike protein implicated in binding. Prior studies on SARS-CoV were then re-analyzed in view of the newly found ABO-related infection risk on SARS-Cov-2. For example, a previous report Chang Y et al (JAMA, 2005) studied 45 health care workers (HCW) in Hong Kong exposed to HK SARS index case and found that SARS-CoV infection risk also differed by ABO types. ABO blood type was significantly associated with SARS, while the O blood group has decreased risk of infection and the A, B, or AB (non-O) groups have about 1.5-fold increased risk of infection (p=0.03). A summary of parts of their results is given in the below Table 3.

TABLE 3

SARS-CoV Infection by ABO blood groups

| Study Groups | Total no. | A | B | AB | All non-O | O (referenced) |
|---|---|---|---|---|---|---|
| Hong Kong SARS-infected HCW | 34 | 8 | 12 | 3 | 23 (88%) | 11 (58%) |
| Hong Kong HCW not infected of SARS | 11 | 0 | 3 | 0 | 3 (12%) | 8 (42%) |

TABLE 3-continued

SARS-CoV Infection by ABO blood groups

| Study Groups | Total no. | A | B | AB | All non-O | O (referenced) |
|---|---|---|---|---|---|---|
| Relative risk (95% CI) | | | | | 1.53 (1.02, 2.3) | 1.0 |
| P-value | | | | | 0.033 | N/A |

Therefore, for both SARS-CoV and SARS-Cov-2 infection, non-O groups have an increased risk compared to the O blood group, which provides about 1.5-fold protection.

Figure 1:
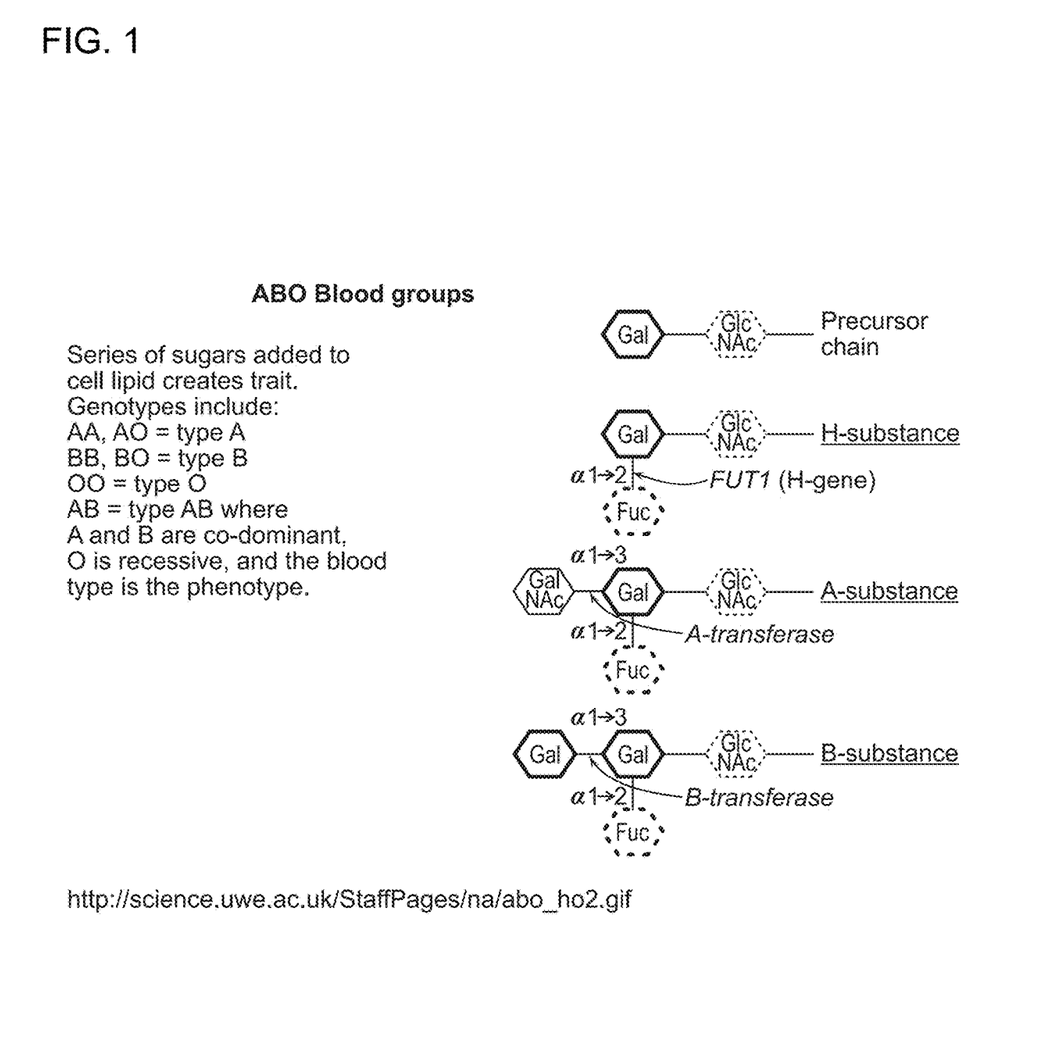
FIG. 1 is a chart showing the ABO blood group system with the presence of one, both, or neither of the A and B antigens on the surface of erythrocytes (red blood cells or RBCs). The precursor oligosaccharide chain ("precursor chain") containing Galactose (Gal) and N-Acetylglucosamine (GlcNAc) is further linked to a fucose (Fuc), by an α(1,2) fucosyltransferase FUT1 enzyme (encoded by H-gene), to form an H antigen ("H-substance"). The H antigen may be further modified with an N-Acetylgalactosamine (GalNAc) or a Galactose (Gal), by an α(1,3) fucosyltransferase enzyme A-transferase or B-transferase, forming an A antigen ("A-substance") or a B antigen ("B-substance"), respectively. RBCs with only one of the H, A, and B antigens are type O, A, or B RBCs, respectively, while RBCs with both the A and the B antigens are type AB RBCs. A subject of the type O or the type AB blood group has the OO or AB genotype, respectively. A subject of the type A (or the type B) blood group may have the AA or AO (or BB or BO) genotype.
Figure 2:
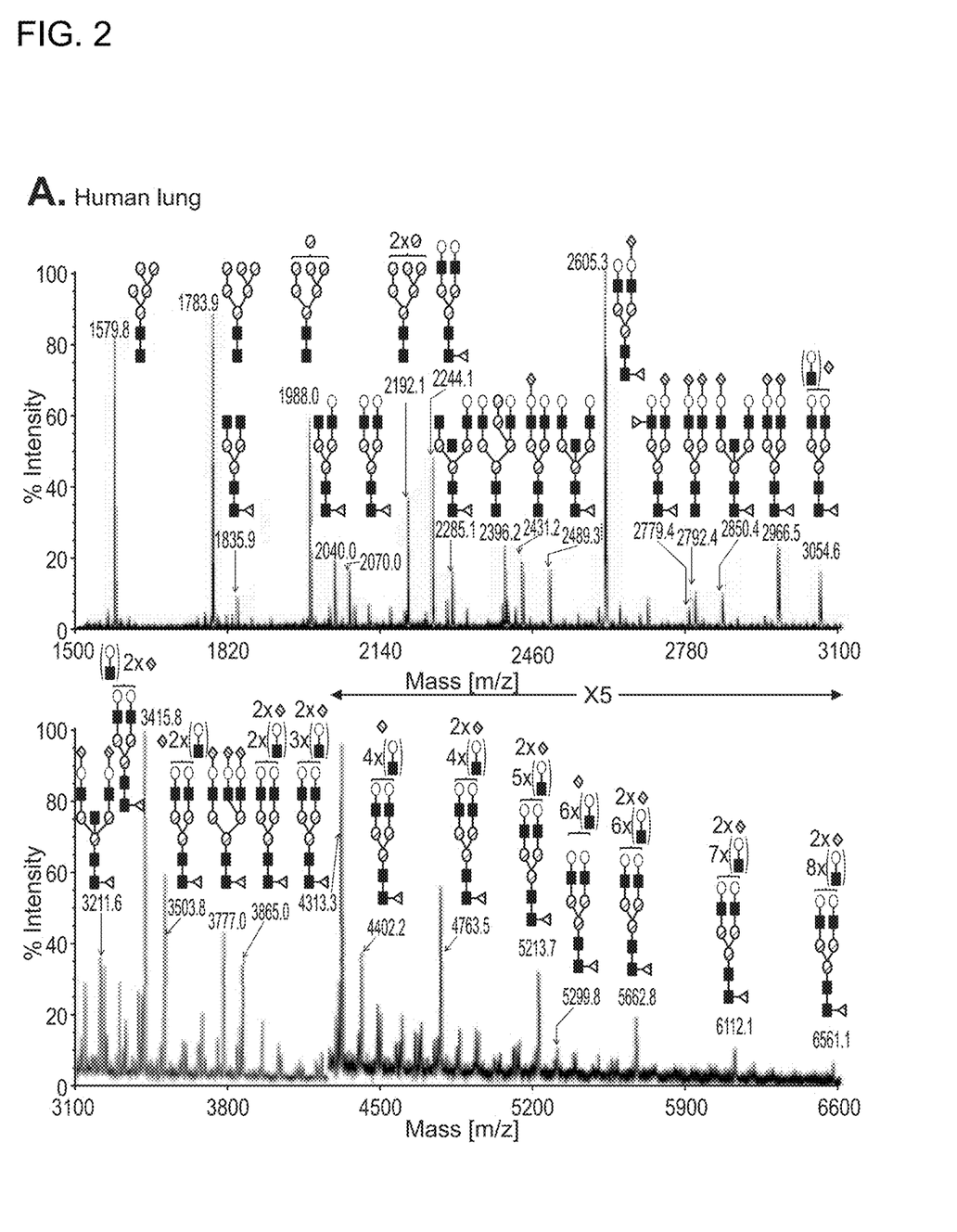

The structures of sugar chains added to lipids on cell surface, representing the differences among the ABO blood groups, are shown in FIG. 1. The increased risk of virus infection for non-O groups may be caused by the additional sugar (e.g., Gal or GalNac) found on cell surface of lung tissue of individuals of the non-O blood group. Presentation of A or B antigen requires another gene FUT2, which controls the ability to attach fucose to the precursor chain. As shown in FIGS. 2A and 2B, there are multiple fucosylated ABO glycans on the surface of human lung and bronchus. The FUT2 gene regulates expression of both H antigen (directly) and A/B blood group antigens (indirectly). For reports on the correlation between the ABO blood groups and the FUT2 function, see Walther et al. (2013) *PLoS Pathog.* 9(3): e1003223. doi: 10.1371/journal.ppat.1003223; and Li et al. (2011) *APJCP* 12(12):3201-3206.

Our re-analysis concluded as follows:

1. ABO risk is similar for SARS-CoV & SARS-CoV-2. For these two types of viruses, non-O blood groups are at similarly increased risk compared to the O blood group, which enjoys about 1.5-fold protection;

2. Such risk has to do with the additional sugar (Gal or GalNAc) found on surface of lung tissue of A or B blood group individuals; and 3. Presentation of the A or B antigen requires another gene (FUT2), which controls the ability to attach fucose to the precursor.

Example 2: A PREVAIL Cohort Study of Epidemiology of Endemic hCoVs in Children

In an ongoing CDC-sponsored PREVAIL cohort study (Morrow, PI), endemic hCoVs have been examined to better understand coronaviruses. Data were collected from a completed respiratory viral panel testing for >12,000 nasal swab samples submitted from Oct. 1, 2017 through Sep. 1, 2019. The Luminex panel detects coronaviruses, adenovirus, bocavirus, enteroviruses/rhinoviruses, influenza, metapneumovirus, RSV and parainfluenza viruses.

Figure 3:
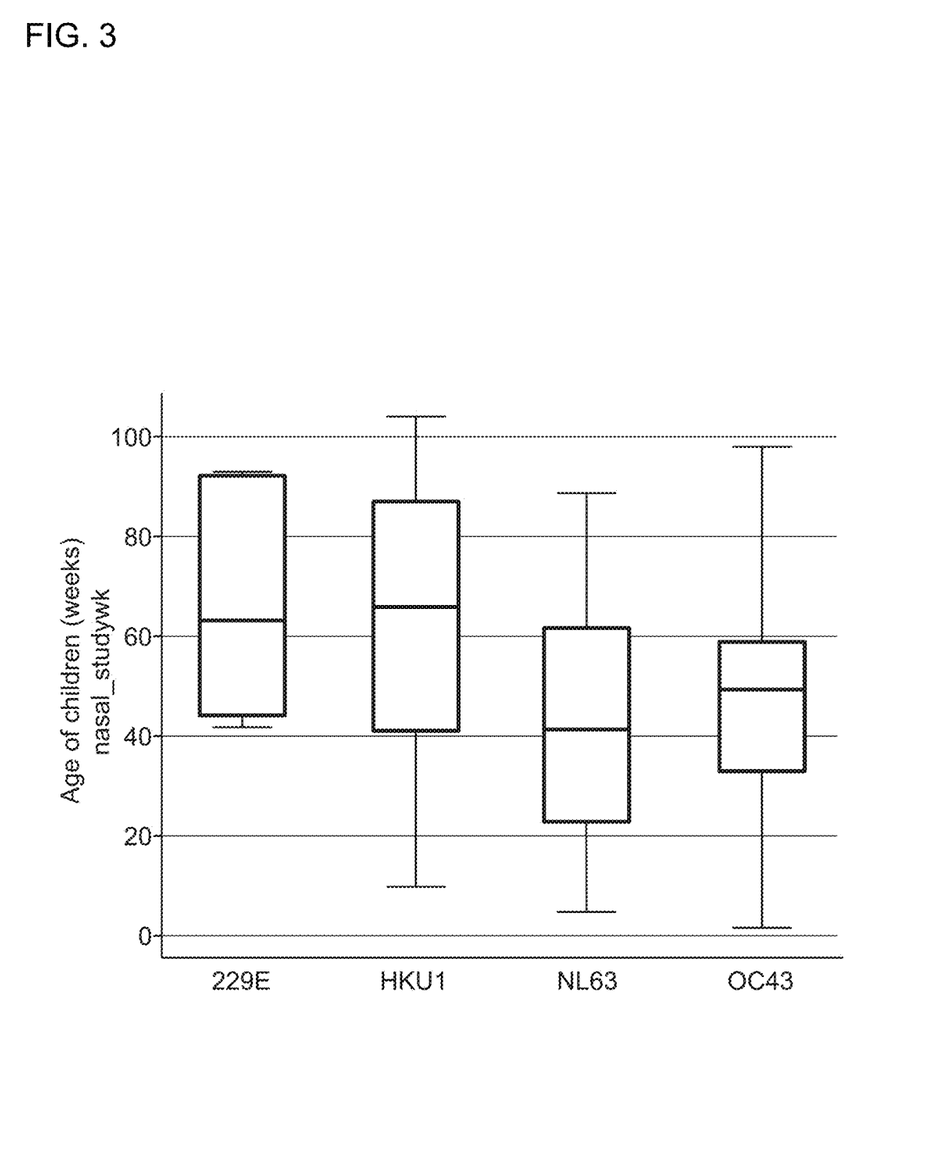
FIG. 3 is a bar chart comparing ages of children infected by various endemic viruses in a PREVAIL cohort study.
Figure 4:
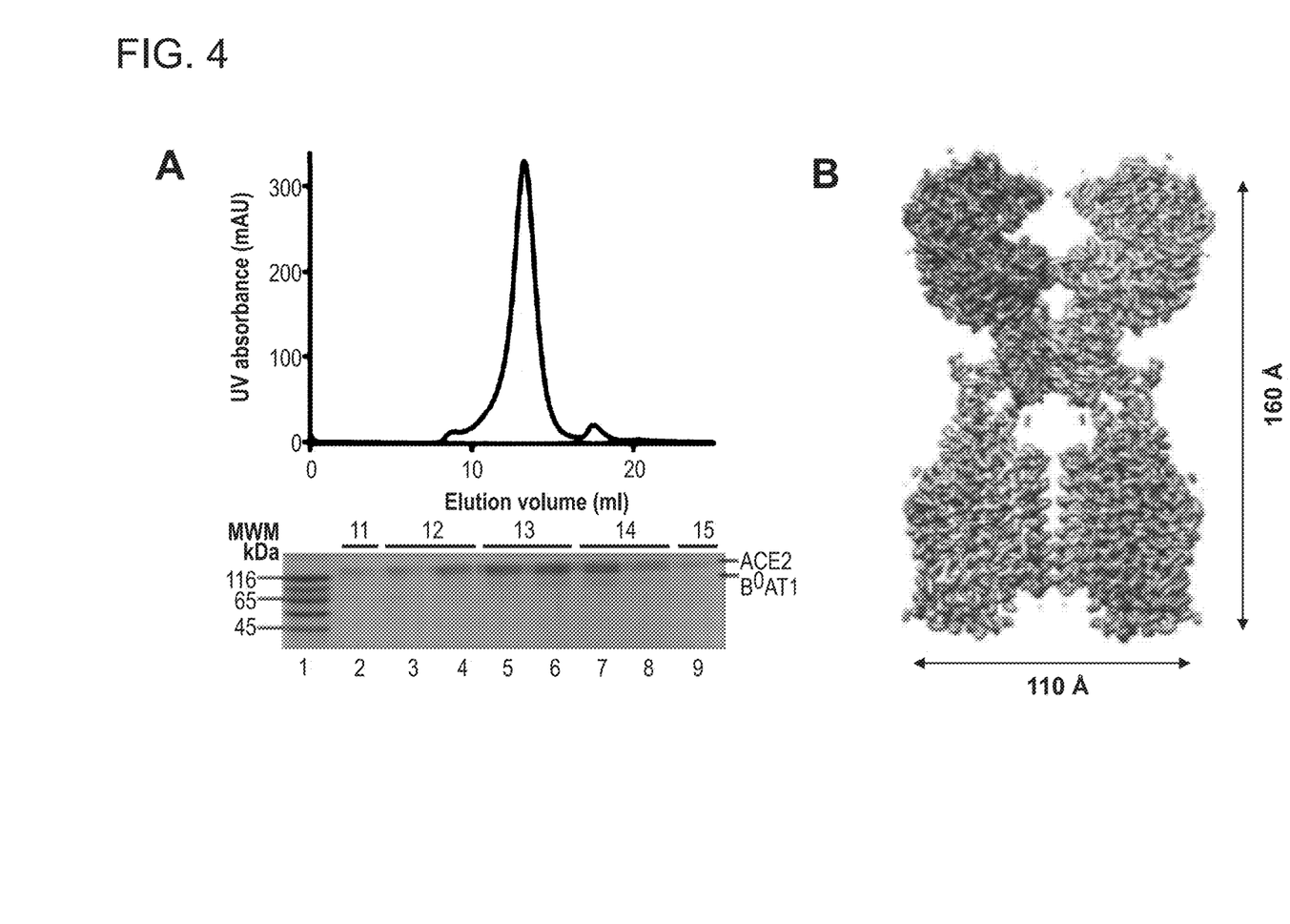
FIGS. 4A-4D are a series of drawings showing the overall structure of the complex between angiotensin-converting enzyme 2 (ACE2) and neutral amino acid transporter B(0)AT1.

Data for four exemplary globally endemic viruses (NL63, OC43, HKU1, and 229E) are shown below. Of the 91 PREVAIL children with ≥75% compliance with weekly nasal swabs, 70 (77%) were positive for a strain of coronavirus at some time. In these 70 coronavirus-positive children, a second infection occurred in nearly 60% of the children. Most repeat infections were with a different strain, but one-quarter of second infections occurred with the same strain. As shown in FIG. 3 and Table 4, there were significant strain-specific differences in carriage by age of child, while NL63 has been more common in infants. Specifically, among the 77% of children ever infected, there were, on average, 2 episodes per child (0-2 yrs). While about 10% of infections were symptomatic, one-third of symptomatic infections were associated with medical care. There were no reported uses of emergency department or hospital. Durations of viral shedding/infection were about 1-4 weeks, depending on strains (p<0.001). Longest duration shedding was with the NL63 strain.

It is hypothesized that secretor status may be relevant to endemic hCoV carriage, but would vary by viral strains. Table 4 below further shows the endemic coronavirus infections in PREVAIL children by FUT2 secretor status. Carriage of strains did vary significantly by secretor status of the child. Infection by the NL63 strain was identified more often in nasal swabs from FUT2 secretors than non-secretors.

TABLE 4

Correlation between virus infection and FUT2 secretor status

| FUT2 status in Children | Total no. | NL63 | OC43 | HKU1 | 229E |
|---|---|---|---|---|---|
| Secretor | 113 (100%) | 40 (35%) | 41 (36%) | 27 (24%) | 5 (4%) |
| Non-secretor | 34 (100%) | 4 (12%) | 17 (50%) | 12 (35%) | 1 (3%) |

P = 0.037 (Fisher's exact)

The PREVAIL data regarding the hCov-NL63 binding and infection may be an important clue for SARS-CoV-2 infection. Human coronavirus NL63 is a species of group 1 coronavirus, identified in 2004 in an infant with bronchiolitis in the Netherlands. HCoV-NL63 has been found worldwide, tending to infect children and immune-compromised individuals and being the etiological agent for up to 10% of all respiratory diseases. The virus is an enveloped, positive-sense, single-stranded RNA virus which enters its host cell by the ACE2 receptor. See Abdul-Rasool et al. (2010) Understanding Human Coronavirus HCoV-NL63. *Open Virol J.* 4:76-84. doi: 10.2174/1874357901004010076. PMID: 20700397; PMCID: PMC2918871. Although SARS-CoV and SARS-CoV-2 are group 2B betacoronaviruses, while NL63 is a group 1 alphacoronavirus, both of them utilize the same ACE2 receptor for attaching and infection. Other coronavirus strains use other receptors. An overview of some known coronavirus entry receptors is in Table 5. See also Wilde et al. (2018) Host Factors in Coronavirus Replication. *Curr. Top. Microbiol. Immunol* 419:1-42.

TABLE 5

Overview of Some Known Coronavirus Entry Receptors

| Genus | Species | Binding partner for the viral S1-NTD | Binding partner for the viral S1-CTD | References |
|---|---|---|---|---|
| Alphacoronavirus | Alphacoronavirus 1 | Neu5Gc and Neu5Ac | APN | Tresnan et al. 1996; Delmas et al. 1992 |
| | PEDV | Neu5Ac | APN | Liu et al. 2015; Li et al. 2007 |
| | PRCV | | APN | Schultze et al. 1996 |
| | HCov-229E | | APN | Yeager et al. 1992 |
| | HCoV-NL63 | | ACE2 | Wu et al. 2009 |
| Betacoronavirus | Betacoronavirus 1 | Neu5,9Ac2 | | Schultze and Herrler 1992; Krempl et al. 1995 |
| | MERS-CoV | | DPP4 | Raj et al. 2013 |
| | MHV | CEACAM1 | | Williams et al. 1991 |
| | HKU1 | Neu5,9Ac2 | | Huang et al. 2015 |
| | HKU4 | | DPP4 | Yang e tal. 2014 |
| | SARS-CoV | | ACE2 | Li et al., 2003 |
| Gammacoronavirus | IBV | Neu5Gc | | Schultze et al. 1993 |
| Deltacoronavirus | PDCV | Unknown | Unknown | |

Abbreviations

S1-NTD: the N-terminal domain of the S1 region of the coronavirus S protein, usually binding to sialic acids, like N-glycolylneuraminic acid (Neu5Gc), N-acetylneuraminic acid (Neu5Ac), and/or 5-N-acetyl-9-O-acetylneuraminic acid (Neu5,9Ac2). One exception is the murine hepatitis virus (MHV) S1-NTD, which binds the N-terminal D1 domain of carcinoembryonic antigen-related cell adhesion molecule 1 (CEACAM1), a type-I membrane protein belonging to the immunoglobulin superfamily;

S1-CTD: the C-terminal domain of the S1 region of the coronavirus S protein, usually binding to aminopeptidase N (APN). Exceptions include HCov-NL63 and SARS-CoV, binding to angiotensin-converting enzyme 2 (ACE2), MERS-CoV and HKU4, binding to dipeptidyl peptidase 4 (DPP4);

PEDV: Porcine epidemic diarrhea virus;
PRCV: Porcine Respiratory coronavirus;
HCoV: Human coronavirus;
MHV: Murine hepatitis virus;
IBV: Infectious bronchitis virus;
PDCV: Porcine delta coronavirus;

REFERENCES

Tresnan et al. (1996) Feline aminopeptidase N serves as a receptor for feline, canine, porcine, and human coronaviruses in serogroup I. *J Virol* 70:8669-8674;

Delmas et al. (1992) Aminopeptidase N is a major receptor for the entero-pathogenic coronavirus TGEV. *Nature* 357: 417-420;

Liu et al. (2015) Receptor usage and cell entry of porcine epidemic diarrhea coronavirus. *J Virol* 89:6121-6125;

Li et al. (2007) Porcine aminopeptidase N is a functional receptor for the PEDV coronavirus. *Virology* 365:166-172;

Schultze et al. (1996) Transmissible gastroenteritis coronavirus, but not the related porcine respiratory coronavirus, has a sialic acid (N-glycolylneuraminic acid) binding activity. *J Virol* 70:5634-5637;

Yeager et al. (1992) Human aminopeptidase N is a receptor for human coronavirus 229E. *Nature* 357:420-422;

Wu et al. (2009) Crystal structure of NL63 respiratory coronavirus receptor-binding domain complexed with its human receptor. *Proc Natl Acad Sci USA* 106:19970-19974;

Schultze and Herrler (1992) Bovine coronavirus uses N-acetyl-9-O-acetylneuraminic acid as a receptor determinant to initiate the infection of cultured cells. *J Gen Virol* 73(Pt 4):901-906;

Krempl et al. (1995) Analysis of cellular receptors for human coronavirus OC43. *Adv Exp Med Biol* 380:371-374;

Raj et al. (2013) Dipeptidyl peptidase 4 is a functional receptor for the emerging human coronavirus-EMC. *Nature* 495:251-254;

Williams et al. (1991) Receptor for mouse hepatitis virus is a member of the carcinoembryonic antigen family of glycoproteins. *Proc Natl Acad Sci USA* 88:5533-5536;

Huang et al. (2015) Human coronavirus HKU1 spike protein uses O-acetylated sialic acid as an attachment receptor determinant and employs hemagglutinin-esterase protein as a receptor-destroying enzyme. *J Virol* 89:7202-7213;

Yang et al. (2014) Receptor usage and cell entry of bat coronavirus HKU4 provide insight into bat-to-human transmission of MERS coronavirus. *Proc Natl Acad Sci USA* 111:12516-12521;

Li et al., (2003) Angiotensin-converting enzyme 2 is a functional receptor for the SARS coronavirus. *Nature* 426:450-454;

Schultze et al. (1993) N-acetylneuraminic acid plays a critical role for the haemagglutinating activity of avian infectious bronchitis virus and porcine transmissible gastroenteritis virus. *Adv Exp Med Biol* 342:305-310.

Example 3: A Structural Study of the Binding Between SARS-CoV-2 and ACE2

The crystal structure for interaction between SARS-CoV-2 and full-length human ACE2 was recently reported [Yan et al. (2020) Structural basis for the recognition of SARS-CoV-2 by full-length human ACE2. *Science* 367: 1444-1448].

The spike glycoprotein (S protein) on the virion surface of SARS-CoV-2 mediates receptor recognition and membrane fusion. During viral infection, the trimeric S protein is cleaved into S1 and S2 subunits and S1 subunits are released in the transition to the postfusion conformation. S1 contains the receptor binding domain (RBD), which directly binds to the peptidase domain (PD) of angiotensin-converting enzyme 2 (ACE2), whereas S2 is responsible for membrane fusion. When S1 binds to the host receptor ACE2, another cleavage site on S2 is exposed and is cleaved by host proteases, a process that is critical for viral infection. The S protein of SARS-CoV-2 may also exploit ACE2 for host infection. A prior publication, Wrapp et al. [*Science* eabb2507 (2020)], reported the structure of the S protein of SARSCoV-2 and showed that the ectodomain of the SARS-CoV-2 S protein binds to the PD of ACE2 with a dissociation constant (Kd) of ~15 nM.

Since the single transmembrane (TM) helix of ACE2 makes it challenging to determine the structure of the full-length protein, Yan et al. used cryo-electron microscopy (cryo-EM) to study the structure of the full-length human ACE2, stabilized by binding to the amino acid transporter B(0)AT1, also known as SLC6A1 (see FIGS. 4A to 4D). Further, a complex between the receptor binding domain (RBD) of SARS-CoV-2 and the ACE2-B(0)AT1 complex was formed and its structure was resolved with an overall resolution of 2.9 Å and with 3.5-Å local resolution at the ACE2-RBD interface.

The overall RBD-ACE2-B(0)AT1 interface is similar to that between SARS-CoV and ACE2, mediated mainly through polar interactions. An extended loop region of the RBD spans the arch-shaped α1 helix of the ACE2-PD like a bridge. The α2 helix and a loop that connects the β3 and β4 antiparallel strands, referred to as loop 3-4, of the PD also make limited contributions to the coordination of the RBD. The contact can be divided into three clusters. The two ends of the bridge interact with the N and C termini of the α1 helix as well as small areas on the α2 helix and loop 3-4. The middle segment of α1 reinforces the interaction by engaging two polar residues.

Structural alignment of the S protein of SARS-CoV-2 with the RBD-ACE2-B0AT1 ternary complex indicates that two S protein trimers can simultaneously bind to an ACE2 homodimer. In addition, the host binding site is highly glycosylated, with seven and five glycosylation sites on each ACE2 and B(0)AT1 monomer, respectively.

Example 4: Reduction of Infection with SARS-CoV-2 (COVID-19), SARS-CoV and Other Major Respiratory Pathogens by Administration of Fucosylated Oligosaccharides SARS-CoV-2 (COVID-19), SARS-CoV, and hCoV-NL63 (an endemic coronavirus strain) bind to the ACE2 receptor, which has many glycosylation sites. It's shown in previous Examples that risk of infections with each of these strains of coronaviruses is increased in individuals with histo-blood group types (e.g., the ABO blood group types) that involve fucosylation. The binding between the viruses and the host ACE2 receptor was enabled or strengthened by A, B, and H antigens in the lung, all of which require an active FUT2 allele for expression. The role of fucosylation in binding or immune response to these coronaviruses is critical.

Preliminary data from the PREVAIL cohort (Morrow, PI) indicate that infection with human coronavirus NL63, one of the major endemic coronavirus strains, differs in frequency between infants depending on their "secretor" histo-blood group type, which is determined by their fucosyltransferase 2 (FUT2) genotype. Secretor histo-blood group type enables expression of ABO fucosylated carbohydrates on the surface of the lung, gut, and in secretions.

All three strains, SARS-CoV, SARS-CoV-2, and hCoV-NL63, use the ACE2 receptor for binding pulmonary mucosa. The ACE2 receptor is heavily glycosylated, an important feature that enables coronavirus binding to this receptor site. It is proposed that A, B, and AB antigens and other fucose-containing glycans are found more abundantly in the ACE2 receptors of individuals who are secretors vs non-secretors.

It's further indicated, not intended to be limiting, that fucosylated receptors participate in or enhance binding of the respiratory pathogens, and that soluble fucosylated oligosaccharide structures can inhibit binding. Preliminary evidence from the PREVAIL cohort shows that the risk of hCoV-NL63 infection was increased two-fold in FUT2+ infants of histo-blood group types A, B, and O. But if the infant has a FUT2+ secretor mother and is being breast-fed, the risk of hCoV-NL63 was reduced 4-fold, indicating that the human milk oligosaccharides inhibit processes that result in infection.

In conclusion, the current studies provide an understanding personal risk of respiratory pathogen infection. The risk in the O blood group type appears one-third lower than the A or B blood group type. In addition, since fucosylated receptors are a critical co-factor in viral binding and infection, similar soluble fucosylated oligosaccharides may be used to competitively inhibit such viral binding and infection.

In an exemplary treatment, 2'-FL, or at least one of other HMOS, is given orally at 1-20 g/day to a subject to reduce infection of the lung. Oral 2'-FL may be administered either by itself in tablet or powder form, or it may be conveniently dissolved in a little water or another beverage, or it may be included in foodstuffs or in food or medical supplements. The preferred 2'-FL adult dose is 10 g per day, but anywhere between 0.2 g per day up to 20 g per day may be taken. 2'-FL is a natural component of human milk and as such it is non-toxic, however high doses (i.e. >10 g per day) may lead to mild gut discomfort and a reversible osmotic diarrhea. Examples of additional fucosylated hMOS which could be used in combination with 2'-FL in the reduction of infection by SARS-CoV-2 (COVID-19), SARS-CoV and other major respiratory pathogens include, but not limited to, 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), and Lacto-N-difucohexaose II (LDFH II).

In another example, 2'-FL, or at least one of other HMOS, is given by inhalation of a powder or aerosol or lavage into the lungs to provide a competitive inhibitor of viral binding to receptor that can reduce cell-surface binding and infection.

In other examples, 2'-FL, alone or mixed with other hMOs, is given by injection into the blood stream of the recipient.

Further, 2'-FL, or at least one of other HMOS, is used to prevent infection (prophylaxis) during times when COVID-19 is prevalent in populations, or to reduce symptomatic infection, or to reduce risk of severe infection (secondary prevention), in a subject.

Clinical trials are designed and performed to test oligosaccharides (such as 2'-FL), either alone or in combination, for their safety and/or effectiveness to improve the overall health of the recipient individual. The recruited individuals may be either healthy or have at least one symptom of diseases and disorders associated with infection by enteric respiratory pathogens (such as COVID-19). Exemplary diseases and disorders may include, at least, acute infectious diarrhea, respiratory tract infection, ear, nose, or throat (ENT) infection, an infectious complication in surgical and critically ill patients, etc. Different individual groups may be set up according to age, sex, health conditions, etc. for treatment.

Various oligosaccharides, such as hMOS, fructo-oligosaccharides (FOS), galacto-oligosaccharides (GOS), and lactulose, may be administered to the recruited individuals for the clinical trials. Different combinations, such as 2'-FL and GOS, may be administered together, or sequentially, to the recruited individuals. The attending physician may decide the appropriate amount and dosage regimen for such single, double, or multiple combinational administrations. For example, the oligosaccharide may be administered between 0.1 g and 10 g, between 0.5 g and 5 g, between 1 g and 5 g, between 1.5 g and 3 g, or in other reasonable or effective amounts according to the individual body weight, every day, every two days, every three days, every week, or in other time periods, for one week, two weeks, three weeks, one month, two months, three months, six months, one year, or any longer periods. The exemplary ratios of two oligosaccharides, such as 2'-FL and another oligosaccharide, for administration are 1:1, 1:2, 1:5, 1:10, 1:100, 100:1, 10:1, 5:1, 2:1, or any ratios found proper or resulting in preferred safety and/or effectiveness readout. Negative controls (e.g., no oligosaccharide or other placebos) and positive controls (e.g., glucose or other sugars) may be used for comparison.

Administration routes may be by oral, anal, inhalation, injection, or other known or acceptable routes to the GI tract, lung, or blood stream of the individuals.

The result of oligosaccharide treatments in the exemplary clinical trials may be gathered by collecting fecal samples of the treated individuals, as described herein or known or acceptable in the art, or other methods to detect the reduction or inhibition of viral infection or binding to cells or tissues of the individuals, or to detect the recovery from at least one symptom related to the viral infection. The readout of the treatment may involve an evaluation of the amount or function of the respiratory pathogen or the amount or function of a biomarker related to viral infection in the treated individual, or general healthy conditions of the treated individuals.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of attenuating or treating a corona virus infection and/or promoting recovery from said corona virus infection in a subject expressing an ACE2 receptor in need thereof, comprising administering to the subject a composition comprising a pharmaceutically effective amount of at least one isolated human milk oligosaccharide (HMO), wherein the corona virus comprises
   i) a severe acute respiratory syndrome virus (SARS-CoV);
   ii) a SARS-CoV-2 (COVID-19) virus; or
   iii) a hCoV-NL63,
   wherein the corona virus binds to the ACE2 receptor on a cell or tissue of the subject, wherein the at least one isolated HMO is identified by structural modeling to compete with the corona virus from binding to the ACE2 receptor on the cell or tissue.

2. The method of claim 1, wherein the at least one isolated human milk oligosaccharide (HMO) is present in an amount effective to reduce or inhibit the corona virus from binding to an animal cell or tissue.

3. The method of claim 1, wherein the at least one isolated human milk oligosaccharide (HMO) comprises 2'-fucosyllactose (2'-FL), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), or Lacto-N-difucohexaose II (LDFH II).

4. The method of claim 1, wherein the composition is in the form of a powder, a tablet, an aerosol, feed for mammalian animals, a packet of sugar, yogurt, a beverage, a weaning food, or an infant formula.

5. The method of claim 2, wherein the binding between the corona virus and the animal cell or tissue is mediated by fucosylation.

6. The method of claim 2, wherein the animal cell or tissue comprises a tissue of a lung or GI tract mucosa or a cell in a tissue of the lung or GI tract mucosa of the subject.

7. The method of claim 1, wherein the subject is a human, non-human primate, mouse, rat, dog, cat, horse, cattle, sheep, pig, chicken, or goat.

8. The method of claim 1, wherein the subject has a fucosyltransferase 2 (FUT2) secretor genotype.

9. The method of claim 1, wherein the subject has an ABO blood group type A, B, or AB.

10. The method of claim 1, wherein said pharmaceutically effective amount is equivalent to a dosage of
i) about 0.2 g to 20 g per day;
ii) about 1 g to 10 g per day; or
ii) about 5 g to 10 g per day.

11. The method of claims 1, wherein the at least one isolated HMO is administered to the lung and/or the GI tract of the subject.

* * * * *